United States Patent [19]

Adolf

[11] Patent Number: 5,317,089
[45] Date of Patent: May 31, 1994

[54] MONOCLONAL ANTIBODIES AGAINST IFN-OMEGA, PROCESSES FOR PREPARING THEM AND THEIR USE IN THE PURIFICATION AND DETECTION OF IFN-OMEGA

[75] Inventor: Günther Adolf, Vienna, Austria

[73] Assignee: Boehringer Ingelheim International GmbH, Fed. Rep. of Germany

[21] Appl. No.: 102,160

[22] Filed: Sep. 28, 1987

[30] Foreign Application Priority Data

Oct. 1, 1986 [DE] Fed. Rep. of Germany ....... 3633323

[51] Int. Cl.$^5$ .................... C07K 15/14; C07K 15/26
[52] U.S. Cl. .................................. 530/351; 530/413; 530/388.23
[58] Field of Search .................... 530/413, 351, 388.23, 530/388.1; 424/85.4, 85.5, 85.1

[56] References Cited

FOREIGN PATENT DOCUMENTS

0170204A2  7/1985  European Pat. Off. .
0174143    3/1986  European Pat. Off. .
0236920A2  3/1987  European Pat. Off. .
WO80/02229 10/1980 PCT Int'l Appl. .
85/5759    2/1986  South Africa .

OTHER PUBLICATIONS

Capon, D. J. et al., *Chem Abstr.* 102:216181g (1985).
Rehberg, E. et al., The Journal of Biological Chemistry 257:11497–11502 (1982).
Stewart, William E. II, The Interferon System, 2d ed., Chapter VII, pp. 134–183, Springer-Verlag, Wien, N.Y. (1981).
Hauptman et al., *Nucleic Acids Research* 13:4739–4749 (1985).
Kearney, et al., *The Jrnl. of Immun.* 123:1548–1550 (1979).

*Primary Examiner*—Jeffrey E. Russel
*Assistant Examiner*—P. Lynn Touzeau
*Attorney, Agent, or Firm*—Sterne, Kessler, Goldstein & Fox

[57] ABSTRACT

The invention relates to new monoclonal antibodies which react specifically with human interferon of the IFN-omega type but not with other human interferons, and processes for preparing them, and for methods for their use in the purification and detection of IFN-omega.

1 Claim, 5 Drawing Sheets

MONOCLONAL ANTIBODIES AGAINST IFN-OMEGA, PROCESSES FOR PREPARING THEM AND THEIR USE IN THE PURIFICATION AND DETECTION OF IFN-OMEGA

FIELD OF THE INVENTION

The present invention relates to methods for preparing monoclonal antibodies against IFN-omega and use of these antibodies in the purification and detection of IFN-omega.

BACKGROUND OF THE INVENTION

*Nucleic Acids Res.* 13:4739–4749 (1985) describes new Type I interferons which differ substantially from the previously known α- and β-interferons with regard to their structure and antigenic properties. This new class of interferon has been designated IFN-omega.

The object of EP-A-0.236.920 (published Sep. 16, 1987) makes it possible to substantially improve the purification of IFN-omega using new monoclonal antibodies, e.g., the new monoclonal antibody OMG-2. These antibodies, however, show specificity for both IFN-α and IFN-omega. It is not possible to conduct an immunoassay for detecting IFN-omega using these antibodies because the level of IFN-omega-specific antibodies in the polyclonal immunoglobulin used as the coating antibody is too low. Moreover, such a test would not be specific for IFN-omega because both the polyclonal and monoclonal antibodies recognize IFN-α.

The detection and quantification of IFN-omega has thus been carried out exclusively via biological testing, for example, by measurement of antiviral activity. Although these detection methods are generally very sensitive, they are time-consuming, laborious and imprecise.

Thus, an immunoassay, such as an ELISA or IRMA test, is needed which could simply, quickly and accurately detect and quantify IFN-omega. Since IFN-omega is present as a monomer in solution, this type of immunoassay would require at least two antibodies capable of recognizing different epitopes of the IFN molecule. For such an assay, the use of monoclonal antibodies would not be essential but would have numerous advantages over antisera.

SUMMARY OF THE INVENTION

The present invention relates to hybridoma cell lines for cultivation in vitro and in vivo and the monoclonal antibodies therefrom which react selectively and specifically with human interferon of the IFN-omega type but not with other human interferons.

In addition, the invention relates to processes for preparing the hybridoma cell line and monoclonal antibodies therefrom, their use in the purification of IFN-omega and in the detection of IFN-omega, for example by means of immunoassays in which these antibodies are specifically used for detecting human interferon of the IFN-omega type. Polyclonal antibodies may additionally be used.

The present invention also comprises an antibody affinity carrier suitable for purifying the omega interferons and processes for preparing it.

It has thus been found, surprisingly, that the problems with the previous immunoassays for IFN-omega can be solved with the aid of the monoclonal antibodies of the present invention. The antibodies prepared according to the invention make it possible to selectively detect and quantify IFN-omega. The monoclonal antibodies of the present invention do not cross-react with other human interferons such as IFN-α, IFN-β, and IFN-gamma.

DESCRIPTION OF THE PREFERRED EMBODIMENTS

Figure 1:
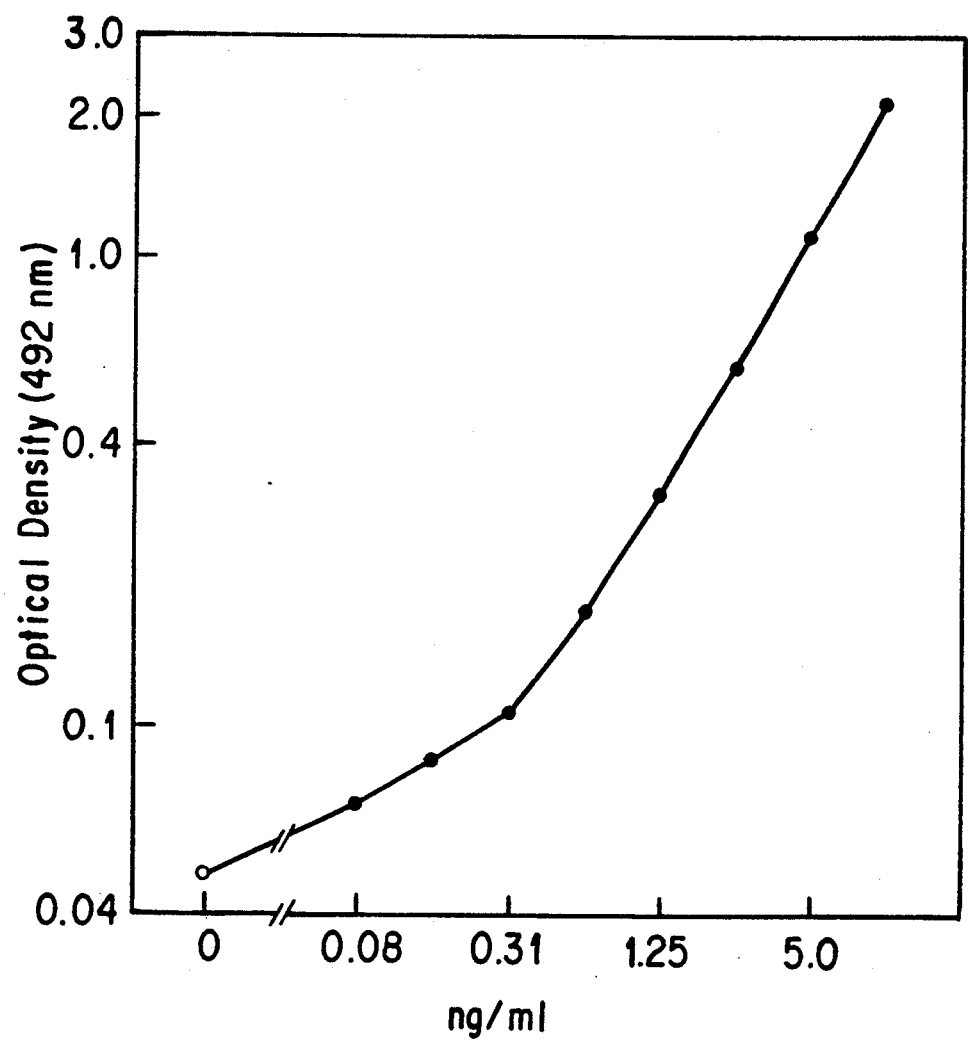
FIG. 1 illustrates the ELISA immunoassay test results for IFN-omega1 in which the coating antibody comprises monoclonal antibody OMG-2 and the peroxidase-antibody conjugate comprises monoclonal antibody OMG-5.

In the method according to the invention, the IFN-omega-specific antibodies are prepared according to the following procedure.

The required antibody-producing hybridoma cell lines are obtained by cell fusion of spleen cells (see Kohler and Milstein in *Nature* 256:495–497 (1975)) from suitably immunized experimental animals (such as mouse spleen cells, with myeloma cells which preferably do not produce antibodies themselves, e.g., myeloma cells of the line P3X63Ag8.653 (see Kearney et al. in *J. Immunol.* 123:1548 (1979)). This process basically consists of injecting mice or other suitable animals with an immunogen. The spleen cells taken from the immunized animals (the sera of which contain antibodies against the injected immunogen) are then fused with myeloma cells. The resulting hybrid cells, or hybridomas, reproduce in vitro.

The hybridoma population is analyzed and manipulated to isolate individual clones from which a single antigen-specific antibody species may be separated. Each individual antibody species obtained in this way is the product of a single B cell from the immunized animal, produced as a reaction to a specific immunogenic structure of the immunogenic substance. Thus, in a living host, an introduced immunogenic substance causes the host immune system to react, forming antibodies to all detectable sites on the immunogenic substance. This formation of antibodies as a defense against the invader involves the production of antibodies of varying affinity and specificity for the immunogenic substance.

In the present invention, experimental animals are immunized with an IFN-omega or a hybrid interferon comprising one part IFN-omega and one part INF-α, preferably comprising IFN-omega1 or IFN-omega1/α2.

The animals are subsequently immunized with IFN-omega, preferably IFN-omega1.

After cell fusion, hybridoma cultures are obtained which are screened to identify those clones which produce antibodies directed against IFN-omega. Biological tests are preferably used to screen the hybridoma, e.g., tests capable of proving the neutralization of the biological activity of an IFN-omega. For example, the antiviral activity of the antibodies might be measured.

Of the five cultures obtained which consistently show a reduction in the antiviral activity of the IFN-omega1 (OMG-4, OMG-5, OMG-6, OMG-7 and OMG-8), clones OMG-4, OMG-5 and OMG-7 were selected for antibody production.

The hybridoma cell lines selected may be cultivated in vitro or in vivo; in vivo culture is preferred. This is accomplished by inoculating the clones into Balb/c mice which have been pretreated with pristane or incomplete Freund's adjuvant (see, for example, Muller et al. in *J. Immunol. Methods* 87:193-196 (1986)). After 7-18 days, the ascites fluid is collected and the antibody is concentrated or isolated from the fluid by precipitation with ammonium sulfate and subsequent affinity chromatography. However, the invention is not intended to be so limited, it being possible to isolate the antibodies using other methods which are known to one of ordinary skill in the art.

Naturally, the desired antibody may be isolated or concentrated analogously from a cell culture supernatant of an in vitro culture.

As previously mentioned, an antibody prepared according to the invention may be used for the purification and detection of IFN-omega, preferably IFN-omega1.

If the antibody obtained according to the invention is to be used for the ultra-purification of IFN-omega, it is preferably covalently bonded to a biologically inactive carrier. The antibody may be covalently bonded to a suitably activated carrier, preferably dextranbased, e.g., CNBr-activated Sepharose or activated CH-Sepharose (Pharmacia, Uppsala).

For ultra-purification, a solution of the omega1 interferon which is to be purified may be obtained either by the processes described in EP-A-0.170.204 or by means of the plasmids described in EP-A-0.236.920 (published Sep. 16, 1987). The omega1 interferon solution is pumped over the antibody affinity carrier thus prepared, at a slightly basic pH, e.g., at pH 7-8, but preferably at pH 7.5, then washed at PH 7.5 until the eluate is free from protein. The bound interferon is subsequently eluted in the acidic pH range, e.g., using 0.1M citric acid in 25% ethylene glycol. The protein-containing fractions thus obtained are subsequently chromatographed over a strongly acidic cation exchanger, e.g., the cation exchanger Mono-S (Pharmacia). The human interferon from the above eluate is immediately adsorbed by the cation exchanger column and subsequently eluted by means of an NaCl gradient.

If the antibodies are to be used in the detection or quantitative determination of an omega interferon, e.g., IFN-omega1 as antigen, conventional immunoassay techniques may be used.

These techniques are based on the formation of a complex between the antigenic substance to be determined and one or more antibodies. One or several parts of the complex may be labelled so that after the complex labelled antigen or antibody has been separated off, it is possible to detect and/or quantitate the antigen.

In the case of a competitive immunoassay technique, the antigenic substance in a liquid sample which is to be investigated competes with a known quantity of antibody binding sites. The quantity of labelled antigen bound to the antibody is therefore in inverse proportion to the quantity of antigen in the sample.

Immunometric methods, on the other hand, use labelled antibodies. In an assay of this kind, the quantity of labelled antibody bound to the complex is proportional to the quantity of antigenic substance contained in the liquid sample.

Since the two-site immunometric assay is based on the formation of an antibody:antigen:antibody sandwich, two different monoclonal antibodies which do not obstruct each other during bonding to the antigen are generally selected.

Immunometric assays are particularly suitable for the detection of polyvalent antigens, i.e., antigenic substances which are capable of forming a complex with two or more antibodies simultaneously. Assays of this kind typically use some quantity of an unlabelled antibody, bound to a solid carrier, which is insoluble in the liquid to be investigated, and a quantity of a soluble antibody which is labelled. Thus it is possible to detect and/or quantitate the amount of the ternary complex which forms between the solid phase antibody, the antigen, and the labelled antibody.

To do this, the antibody bound to the solid phase is generally first brought into contact with the sample being investigated so that the antigen can be extracted from the sample by forming a binary solid phase antibody:antigen complex. After a suitable incubation period, the solid carrier is washed to remove the residues of the liquid probe, including any unreacted antigen which may be present. It is then contacted with a solution which contains a known quantity of the labelled antibody.

A second incubation period allows the labelled antibody to complex with the antigen which is bound to the solid carrier by the unlabelled antibody. The solid carrier is washed a second time in order to remove any unreacted unlabelled antibody. In a simple "Yes/No" assay to determine whether or not there is any antigen in the sample, the washed solid carrier is investigated. The quantity of labelled antibody detected is compared with that of a negative control sample which is free of the antigen. The detection of labelled antibody in quantities considerably higher than background level, represented by a negative control, indicates the presence of the suspected antigen.

Quantitative detection is possible by comparison with samples containing known quantities of the antigen.

In the previously described assays, for example, the carrier may be a conventional carrier such as glass, polystyrene, polypropylene, polyethylene, dextran, nylon, amylase, natural or chemically modified cellulose, polyacrylamide, agarose or magnetite. The markers in the assays may be enzymes, radioisotopes, metal chelates or fluorescent, chemiluminescent or bioluminescent compounds.

Examples of enzymes which may be used include malate dehydrogenase, Staphylococcal nuclease, delta-5-steroid isomerase, α-glycerol phosphate dehydrogenase, triosephosphate isomerase, horseradish peroxidase, alkaline phosphatase, asparaginase, glucose oxidase, β-galactosidase, ribonuclease, urease, catalase, glucose-6-phosphate dehydrogenase, glucoamylase or acetylcholinesterase.

The radioisotope used may be $^3H$, $^{125}I$, $^{127}I$, $^{32}P$, $^{35}S$ and $^{14}C$.

The fluorescent compounds may be fluorescein isothiocyanate, rhodamine, phycoerythrin, phycocyanin, allophycocyanin, o-phthaldehyde or fluorescamine.

The chemiluminescent compounds may be luminol, isoluminol, an aromatic acridinium ester, imidazole, an acridinium salt or an oxalic acid ester.

The bioluminescent compounds may be luciferin, luciferase or aequorin.

Moreover, an antibody according to the invention may be linked to a low molecular hapten such as biotin, dinitrophenyl, pyridoxal or fluorescamine. These haptens may then be recognized by a further specific reaction, such as biotin with the aid of avidin, or fluorescamine with the aid of a specific antihapten antibody.

Moreover, the activity of an enzyme used as a marker may be used to intensify the signal which is being measured.

It is particularly preferred to use horseradish peroxidase as the marker because this enzyme is capable of reacting with numerous substrates. Moreover, it is relatively small and can easily be linked to an antibody, for example by the periodate method.

The preferred methods of detecting or quantitatively determining an omega interferon, preferably IFN-omegal, are, if the IFN-omega is radioactively labelled, competitive radioimmunoassay (RIA) in which polyclonal antibodies or antibody sera are used, in particular, immunoradiometric assay (IRMA) if the antibody is radioactively labelled, and "enzyme-linked immunosorbent assay" (ELISA) if the antibody is labelled with an enzyme.

According to the invention, IFN-omega, but preferably IFN-omegal, is detected or quantitated in a test liquid as follows:

a) by contacting the sample to be investigated with a carrier, to which a polyclonal or monoclonal antibody against the IFN-omega to be determined, is bound, and b) by measuring the formation of the binary complex formed under a) with formation of a ternary complex between a labelled monoclonal antibody and the binary complex formed according to a).

The omega interferons needed to carry out this invention are disclosed in EP-A-0.170.204. The monoclonal antibodies, e.g., antibody OMG-2, which are not described in the present invention, as well as the hybrid interferons used for immunization, are disclosed in EP-A-0.236.920 (published Sep. 16, 1987). The polyclonal antibodies used in the practice of the invention may be obtained using methods known from the literature.

The following examples are illustrative but do not limit the methods and compositions of the present invention. Other suitable modifications and adaptations which are known to those of ordinary skill in the art are within the spirit and scope of the invention.

EXAMPLES

Example 1

Preparation of monoclonal antibodies specific to IFN-omega a) Immunization

A female Balb/c mouse about 8 weeks old was immunized with highly purified (purity>95%) hybrid interferon IFN-omegal/α2 as follows:

1st immunization: 200 mcg in complete Freund's adjuvant, by intraperitoneal route 2nd immunization: 200 mcg in complete Freund's adjuvant, by intraperitoneal route, 5 weeks after the 1st immunization Eight months after the second immunization, the mouse was immunized again with 70 mcg of purified IFN-omegal (purity>90%) (incomplete adjuvant, intraperitoneal route). Twelve days later a serum sample was taken. Neutralization tests showed that the mouse's serum now contained relatively high titres of neutralizing antibodies against IFN-omegal (total neutralization at up to 1000-fold dilution of the serum, partial neutralization at 10,000-fold dilution). The neutralization test was carried out as follows: 100 mcl of a dilution of the serum sample in cell culture medium was mixed with 100 mcl of a solution of IFN-omegal (100 antiviral units/ml) and incubated for 90 minutes at 37° C. The antiviral activity of the samples was then tested in a biological test (A549 lung cancer cells, encephalomyocarditis virus). Five weeks after the third immunization, the mouse was injected with another 70 mcg of purified IFN-omegal (purity>90%) without any adjuvant.

b) Production and screening of hybridomas

Hybridomas were produced using the method originally developed by Kohler and Milstein (*Nature* 256:495 (1975)) using the non-secreting cell line P3X63Ag8.653 (Kearney et al., *J. Immunol.* 123:1548 (1979)). The following procedure was used:

Four days after the last immunization (see above), the mouse's spleen was removed. The spleen cells were mechanically freed from the connecting tissue, suspended in cell culture medium (RPMI 1640 medium with added sodium penicillin G (100 units/ml) and streptomycin sulfate (50 units/ml) and collected by centrifuging (Beckmann TJ-6 centrifuge, 10 minutes at 1000 rpm). $2 \times 10^8$ myeloma cells (cultivated in cell culture medium as above with the addition of 10% fetal calf serum) were also collected by centrifuging and washed once with serum-free cell culture medium. Finally, the spleen cells and myeloma cells were resuspended in serum-free cell culture medium, combined, and centrifuged again. The supernatant was removed and the cells were suspended in 3 ml of fusion medium (45% RPMI 1640 medium, 50% polyethylene glycol 4000, 5% dimethylsulfoxide). They were carefully shaken for 90 seconds, then left to stand for a further 60 seconds. 3 ml of serum free culture medium was then added dropwise over a period of 90 seconds and left to stand for 60 seconds. A further 6 ml of serum free culture medium was added dropwise over a period of 90 seconds. Finally, 12 ml of culture medium containing 10% fetal calf serum was slowly added with constant stirring and left to stand for 10 minutes. The mixture was then made up to 50 ml with cell culture medium containing 10% fetal calf serum. The cells were collected by centrifuging and suspended in 400 ml of cell culture medium with the addition of 20% fetal calf serum and hypoxanthine ($10^{-4}M$), aminopterin ($4 \times 10^{-7}M$) and thymidine ($1.6 \times 10^{-5}M$), hereinafter referred to as HAT medium. Peritoneal macrophages from Balb/c mice were also added to this suspension (about 50,000/ml). The suspension was finally pipetted into cell culture plates (48 wells per plate; 0.5 ml per well) and incubated at 37° C. (95% air, 5% $CO_2$, saturated water vapor). After 3 days, 0.5 ml of HAT medium was added to each culture. Of the 800 cultures set up, approximately 300 cultures showed some growth of hybridoma cells after two to three weeks.

The subsequent screening was carried out as follows:

Culture supernatant of at least 10–20% confluent hybridoma cultures were mixed with equal volumes of a solution of HuIFN-omega1 (20 antiviral units/ml), incubated for 90 minutes at 37° C. and then tested for their antiviral activity. All cultures were tested at least twice at intervals of one week. Five of the cultures, designated OMG-4, OMG-5, OMG-6, OMG-7 and OMG-8, consistently showed a reduction in antiviral activity in all tests. All the cultures were cloned by limiting dilution and the clones were tested again for any neutralizing activity using the method described above. From each culture, 3–5 positive clones were pooled. In order to produce antibodies in vivo from each of the hybridoma cultures, $3-10 \times 10^6$ cells were inoculated by intraperitoneal route into Balb/c mice which had been intraperitoneally injected, two to three days earlier, with 0.5 ml of incomplete Freund's adjuvant, or with 0.5 ml of pristane, seven to ten days earlier. After seven to 21 days, the ascites fluid formed was recovered. The antibodies contained in the ascites fluid were concentrated to a purity of over 90% by precipitation with 50% ammonium sulfate and affinity chromatography over carrier-bound protein A by known methods. For each ml of ascites fluid, about 2–5 mg of pure antibodies were obtained from all the hybridomas.

c) Characterization of the antibodies OMG-4, OMG-5 and OMG-7

The antibodies were examined by sodium dodecylsulfate-polyacrylamide electrophoresis under non-reducing conditions and gel permeation high pressure liquid chromatography. All antibodies showed retention characteristics identical to those of an IgG marker protein and are therefore of the IgG type. In a neutralization test in which the inhibition of antiviral activity of interferons was investigated (see above), all of the antibodies neutralized the activity of IFN-omega1 at a concentration of 100 mcg/ml but did not neutralize the activity of IFN-α2c, IFN-β or IFN-gamma.

These three clones were deposited on Aug. 14, 1987, according to the Budapest Treaty at the European Collection of Animal Cell Cultures, PHLS Centre for Applied Microbiology and Research, Porton Down, Salisbury, Wiltshire SP4 OJG, United Kingdom, under the ECACC accession numbers 87 081401 (OMG-4), 87 081402 (OMG-5) and 87 081403 (OMG-7).

Example 2

Enzyme immunoassays (ELISA) for IFN-omega1

The antibodies OMG-5 and OMG-7 were covalently bound to horseradish peroxidase using known methods (see, for example, Wilson, M. B. and Nakane, P. K., in *Immunofluorescence and Related Staining Techniques*, published by W. Knapp et al., pp. 215–224; Elsevier 1978). The procedure used was as follows: 2 mg of horseradish peroxidase in water was mixed with 0.2 ml of 100 mM sodium periodate and shaken for 40 minutes at ambient temperature, then dialyzed against $2 \times 500$ ml of 1 mM sodium acetate, pH 4.4, overnight at 4° C. The solution was then adjusted to a pH of about 9 using 0.1M NaHCO$_3$ at pH 9.5. A solution of the monoclonal antibody (1.6 mg/ml with 2 ml of OMG-5 or 4.7 mg/ml with 1.5 ml of OMG-7; each in 10 mM NaHCO$_3$ at pH 9.5) was added to this solution and the resulting mixture was shaken for 2 hours at ambient temperature. 100 mcl of a solution of NaBH$_4$ (4 mg/ml in water) was added and the solution incubated in an ice bath for another 2 hours. 3 ml of cold saturated ammonium sulfate solution was then added dropwise and the mixture was incubated for another hour in an ice bath. The precipitate of peroxidase-immunoglobulin conjugate formed was collected by centrifuging, dissolved in 1 ml of phosphate-buffered isotonic saline solution at pH 7.4, and stabilized by the addition of 1 ml of a solution of bovine serum albumin (10 mg/ml) in phosphate-buffered saline solution). The solution was frozen at $-70°$ C.

Solid phase sandwich enzyme immunoassays for IFN-omega1 were carried out using generally known methods (see, for example, Berthold, W., Merk, W., and Adolf, G. R., *Arzneim.-Forschung./Drug Res.* 35:364–369 (1985)). In order to coat the microtiter ELISA test plates, the monoclonal antibodies OMG-2, OMG-5 or OMG-7 were used in a concentration of 10 mcg/ml in 0.1M sodium carbonate at pH 9.5 (100 mcl per well). The plates were incubated either for one hour at ambient temperature or overnight at 4°–8° C. The antibody solution was removed, the wells were each washed with 200 mcl of water and filled with 100 mcl of a solution of bovine serum albumin (5 mg/ml) in phosphate-buffered isotonic saline solution at pH 7.4 (hereinafter referred to as PBS/BSA). 100 mcl of a solution of IFN-omega1 in a concentration of 20 ng/ml was then added and mixed, and a series of dilutions was produced by serial transfers of 100 mcl. Finally, 50 mcl of a solution of the antibody-enzyme conjugate (OMG-5/peroxidase or OMG-7/peroxidase, original solution (see above), 1:10,000 dilution in PBS/BSA) was added to all the wells and the plates were incubated for 3 hours at ambient temperature. The solution was then removed, the wells were washed three times with water and each was filled with 100 mcl of substrate solution (3 mg/ml ortho-phenylenediamine and 1 mg/ml sodium perborate in 0.067M potassium citrate at pH 5). After incubation for 30 minutes at ambient temperature, 100 mcl of 4N sulfuric acid was pipetted into each well. The optical density at 492 nm was then measured in a multi-channel photometer (ELISA reading apparatus).

Figure 2:
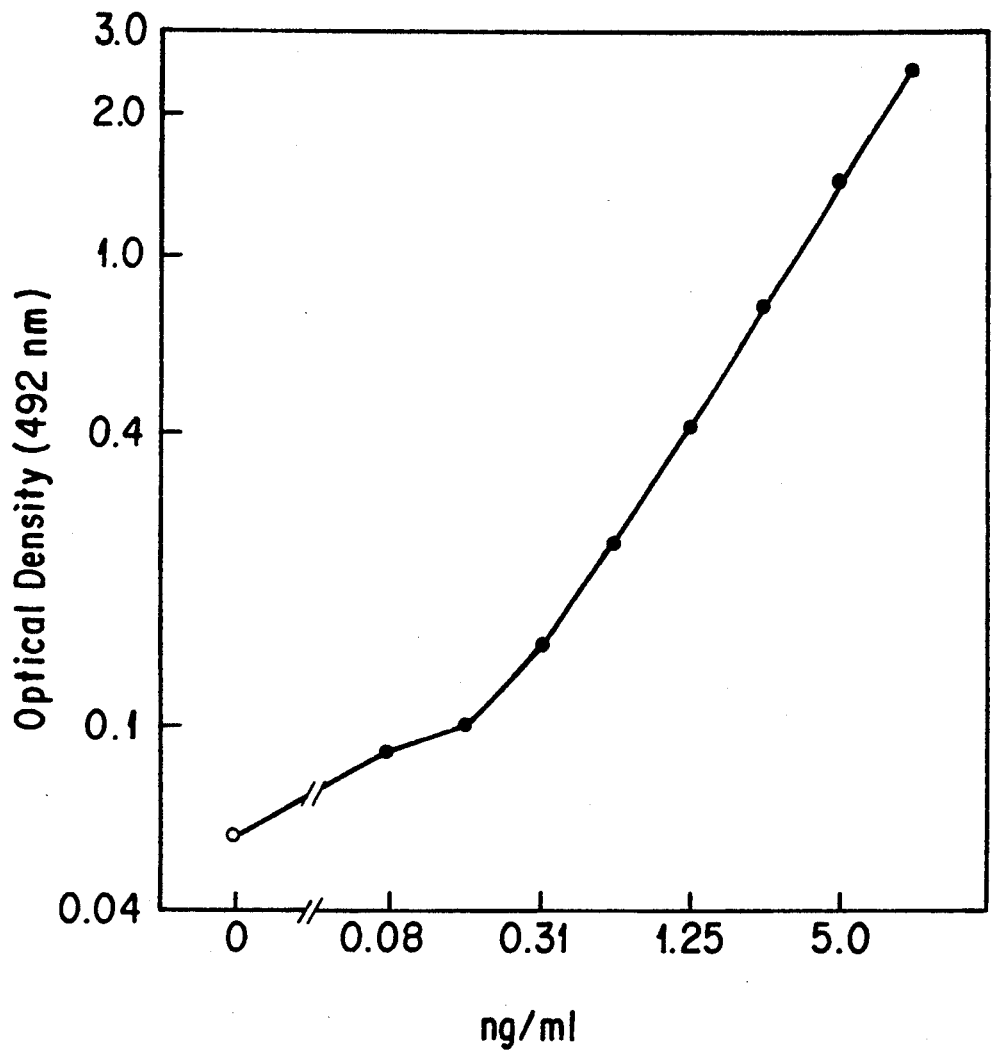
FIG. 2 illustrates the ELISA immunoassay test results for IFN-omega1 in which the coating antibody comprises monoclonal antibody OMG-2 and the peroxidase-antibody conjugate comprises monoclonal antibody OMG-7.
Figure 3:
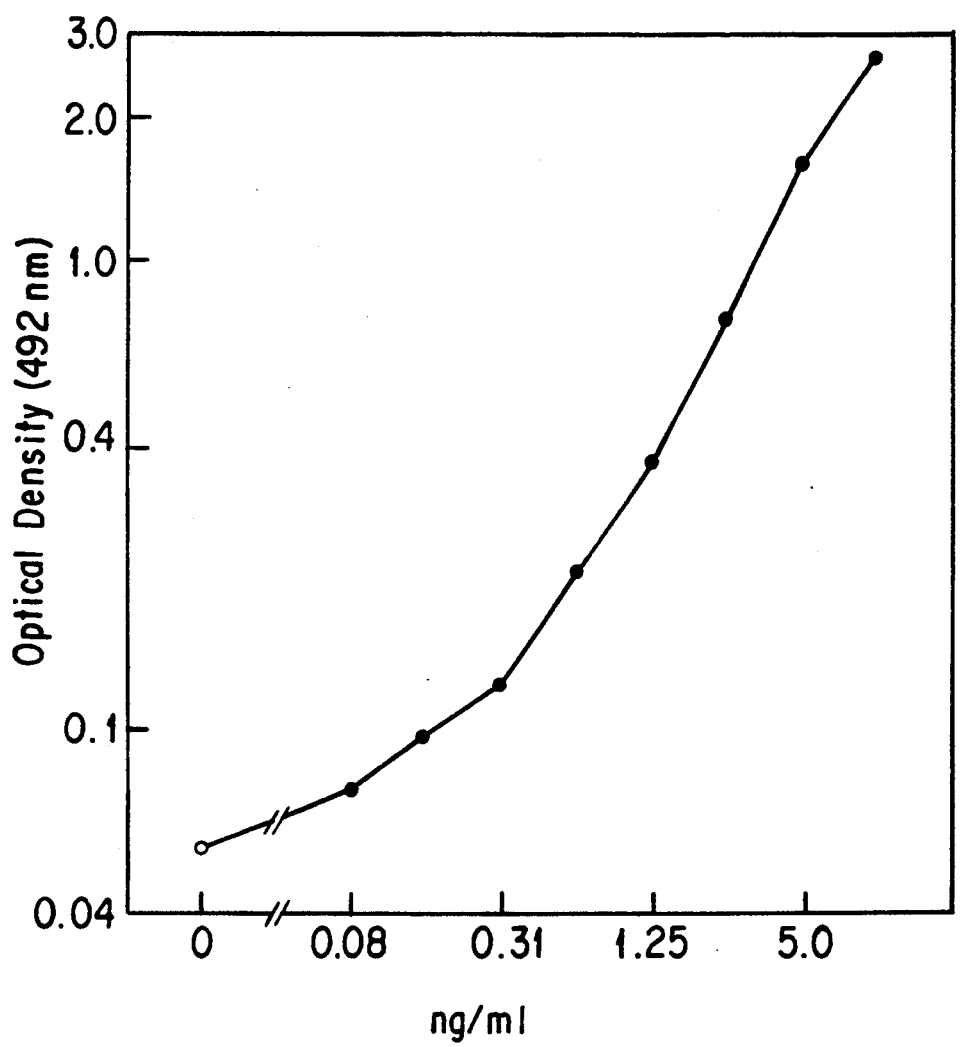
FIG. 3 illustrates the ELISA immunoassay test results for IFN-omega1 where the coating antibody comprises monoclonal antibody OMG-5 and the peroxidase-antibody conjugate comprises OMG-7.

Dosage-dependent changes in absorption were achieved with all the heterologous combinations of coating antibodies and antibody-peroxidase conjugate. FIGS. 1, 2 and 3 show the curves obtained.

Figure 4:
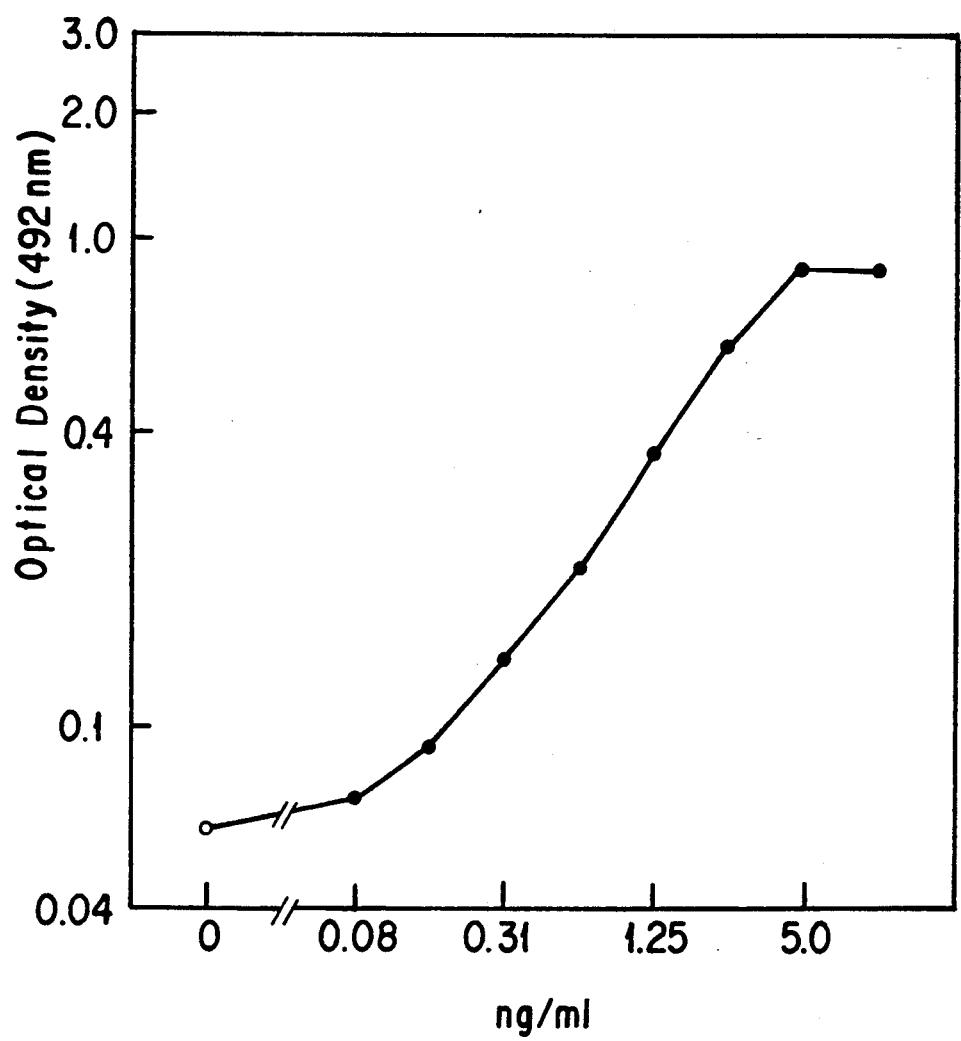
FIG. 4 illustrates the ELISA immunoassay test results for IFN-omega1 in which the coating antibody comprises rabbit anti-IFN-omega1 immunoglobulin and the peroxidase-antibody conjugate comprises monoclonal antibody OMG-7.

Coating may also be carried out using a rabbit anti-IFN-omega1 immunoglobulin obtained by twice immunizing a rabbit with IFN-omega1 and partial purification from the serum by precipitation with 50% ammonium sulfate in a concentration of 10 mcg/ml (see FIG. 4).

The specificity of the ELISA (see FIG. 2) for IFN-omega constructed from the antibody OMG-2 (see EP-A-0.236.920) and peroxidase-bound antibody OMG-7 was tested by applying preparations of other human interferons over a very wide range of concentrations. Examples of the interferons used are listed below:

| Interferon | Source | Concentration Range |
|---|---|---|
| IFN-α1 | recombinant (*E. coli*) | 2 ng–50 mcg/ml |
| IFN-α2c | recombinant (*E. coli*) | 2 ng–50 mcg/ml |
| IFN-αB | recombinant (*E. coli*) | $3 \times 10^2$–$1.25 \times 10^6$ E/ml |
| IFN-αF | recombinant (*E. coli*) | $1.4 \times 10^1$–$3.5 \times 10^5$ E/ml |
| IFN-β | fibroblasts, induced with Poly (I:C) | $8 \times 10^2$–$2 \times 10^6$ E/ml |
| IFN-gamma | recombinant (*E. coli*) | 2 ng–50 mcg/ml |

At a sensitivity of 100 pg/ml for IFN-omega1, no significant signal was observed with any of the preparations at any concentration. The ELISA can therefore be used not only to quantify recombinant IFN-omegal but also, for example, to determine the proportion of IFN-omegal in leukocyte interferon or other interferon preparations obtained from cell cultures.

Example 3

Immunoradiometric assay (IRMA) for IFN-omegal

The antibody OMG-7 was radioactively labelled using a known method with N-succinimidyl[2,3-$^3$H] propionate ($^3$H-NSP, Amersham International, England; 110 Ci/mmol). 1 mCi of the solution of $^3$H-NSP was dried in vacuo in a siliconized test vessel. 50 mcg of a solution of the monoclonal antibody OMG-7 (4.7 mg/ml) in buffered saline solution at pH 7.4 was pipetted into the vessel and 3 mcl of 1M borate buffer at pH 8.5 was then added. After 24 hours at 4° C., the excess $^3$H-NSP was reacted with 20 mcl of 1M glycine in borate buffer and diluted with 250 mcl of 50 mM potassium phosphate buffer at pH 7.4, 150 mM NaCl and 5 mg/ml of bovine serum albumin. It was then separated from the labelled antibody over a Sephadex G 50M column (0.5×20 cm). The antibody showed a specific activity of about 10 Ci/g of protein.

Figure 5:
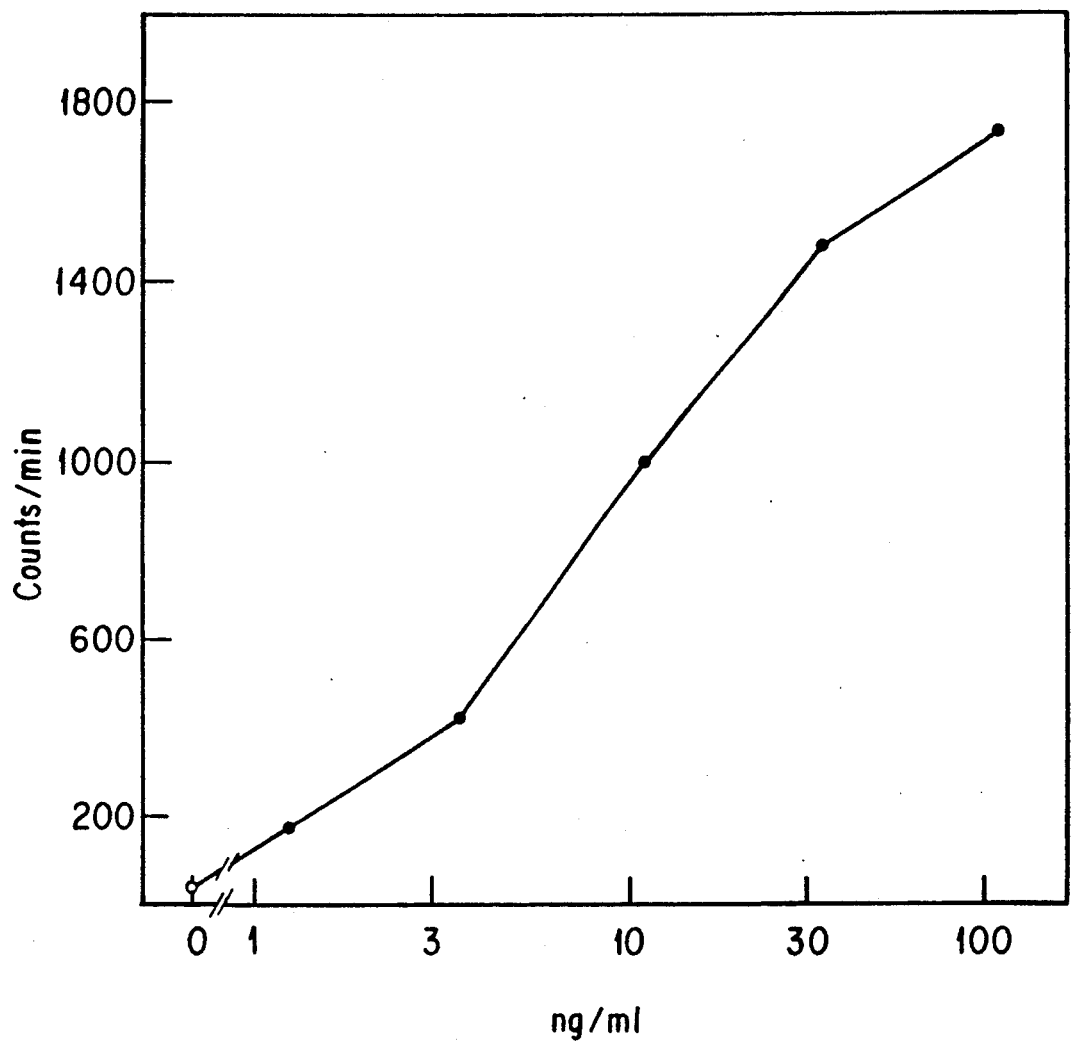
FIG. 5 illustrates an immunoradiometric assay for HuIFN-omega1 in which the bound radioactivity is a function of the interferon concentration.

In order to carry out the test, etched polystyrene pellets (diameter 6.5 mm; Northumbria Biologicals of England) were coated with the antibody OMG-2 (10 mcg/ml in 0.1M sodium carbonate at pH 9.5 for 1 hour at ambient temperature) . The pellets were then incubated for 1 hour in PBS/BSA (see Example 2) and washed twice with 250 mcl of water. The pellets were incubated in suitable test tubes with 200 mcl of a solution of IFN-omegal in increasing concentrations in PBS/BSA for 3 hours at 4° C. and washed three times with 250 mcl of water. 200 mcl batches of a solution of the labelled antibody (100 ng/ml in PBS/BSA; about 27,000 counts/minute/test tube) was then added and the resulting mixture was incubated for 20 hours at 4° C. The pellets were then washed three times with 20 mcl of water and transferred to polypropylene tubes. The bound radioactivity was measured in a liquid scintillation counter after the addition of 4 ml of scintillation cocktail. FIG. 5 shows the bound radioactivity as a funtion of the interferon concentration.

What is claimed is:

1. A method for the purification of omega interferon, comprising:
    (a) contacting a sample suspected of containing said omega interferon with a monoclonal antibody which neutralizes the activity of an omega interferon but does not neutralize the activity of IFN-$\beta$, IFN-$\gamma$ or $\alpha$-interferons to form a complex;
    (b) separating said complex formed in step (a); and
    (c) recovering said omega interferon.

* * * * *